(12) United States Patent
Gdaniec et al.

(10) Patent No.: US 11,241,162 B2
(45) Date of Patent: Feb. 8, 2022

(54) METHOD OF IMPROVED MULTIPLE-PHASE DYNAMIC CONTRAST-ENHANCED MAGNETIC RESONANCE IMAGING WITH MOTION CORRECTION USING WATER/FAT SIGNAL SEPARATION

(71) Applicants: KONINKLIJKE PHILIPS N.V., Eindhoven (NL); UNIVERSITY OF TEXAS SOUTHWESTERN MEDICAL CENTER, Dallas, TX (US)

(72) Inventors: Nadine Gdaniec, Eindhoven (NL); Peter Boernert, Eindhoven (NL); Mariya Ivanova Doneva, Eindhoven (NL); Ivan Pedrosa, Eindhoven (NL)

(73) Assignees: Koninklijke Philips N.V., Eindhoven (NL); Board of Regents of the University of Texas Systems, Austin, TX (US)

( * ) Notice: Subject to any disclaimer, the term of this patent is extended or adjusted under 35 U.S.C. 154(b) by 1120 days.

(21) Appl. No.: 15/303,535

(22) PCT Filed: Mar. 31, 2015

(86) PCT No.: PCT/IB2015/052354
§ 371 (c)(1),
(2) Date: Oct. 12, 2016

(87) PCT Pub. No.: WO2015/159172
PCT Pub. Date: Oct. 22, 2015

(65) Prior Publication Data
US 2017/0027472 A1    Feb. 2, 2017

Related U.S. Application Data

(60) Provisional application No. 61/980,668, filed on Apr. 17, 2014.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/4869* (2013.01); *A61B 5/7207* (2013.01);
(Continued)

(58) Field of Classification Search
CPC ..... A61B 5/055; A61B 5/4872; A61B 5/7207; A61B 5/4869; G06T 7/30; G06T 7/0012;
(Continued)

(56) References Cited

U.S. PATENT DOCUMENTS

| | | | |
|---|---|---|---|
| 2003/0117136 A1* | 6/2003 | Wang | G01R 33/5676 324/306 |
| 2006/0045366 A1* | 3/2006 | Chefd'hotel | G06T 7/207 382/236 |

(Continued)

FOREIGN PATENT DOCUMENTS

WO    WO-2014154544 A1 * 10/2014

OTHER PUBLICATIONS

Ma et al "Fat-Suppressed Three-Dimensional Dual Echo Dixon Technique for Contrast Agent Enhanced MRI" Journal of Magnetic Resonance Imaging 23 (2006) p. 36-41.
(Continued)

*Primary Examiner* — Bill Thomson
*Assistant Examiner* — Aminah Asghar

(57) ABSTRACT

A method of operating a magnetic resonance imaging system (10) with regard to acquiring multiple-phase dynamic contrast-enhanced magnetic resonance images, the method comprising steps of acquiring (48) a first set of magnetic resonance image data ($x_{pre}$) prior to administering a contrast
(Continued)

agent to the subject of interest (20), by employing a water/fat magnetic resonance signal separation technique, determining (52) a first image of the spatial distribution of fat ($I_{pre}$) of at least the portion of the subject of interest (20), acquiring (50) at least a second set of magnetic resonance image data ($x_2$) of at least the portion of the subject of interest (20) after administering the contrast agent to the subject of interest (20), by employing a water/fat magnetic resonance signal separation technique, determining (54) at least a second image of the spatial distribution of fat ($I_2^{ph}$) of at least the portion of the subject of interest (20), applying (56) an image registration method to the second image of the spatial distribution of fat ($I_2^{ph}$) with reference to the first image of the spatial distribution of fat ($I_{pre}$) for correcting a potential motion of the subject of interest (20); and a magnetic resonance imaging system (10) having a control unit (26) that is configured to carry out steps (56-64) of such a method; and a software module (44) for carrying out such a method, wherein the method steps (56-64) to be conducted are converted into a program code that is implementable in a memory unit (30) and is executable by a processor unit (32) of the magnetic resonance imaging system (10).

9 Claims, 2 Drawing Sheets

(51) Int. Cl.
    *G01R 33/565*        (2006.01)
    *G06T 7/00*            (2017.01)
    *G01R 33/563*        (2006.01)
    *G01R 33/56*          (2006.01)
    *G01R 33/48*          (2006.01)

(52) U.S. Cl.
    CPC ... *G01R 33/4828* (2013.01); *G01R 33/56509* (2013.01); *G06T 7/0012* (2013.01); *A61B 5/4872* (2013.01); *G01R 33/5601* (2013.01); *G01R 33/56366* (2013.01); *G06T 2207/10088* (2013.01); *G06T 2207/30096* (2013.01)

(58) Field of Classification Search
    CPC .......... G06T 2207/30096; G06T 2207/10088; G01R 33/5601; G01R 33/4828
    See application file for complete search history.

(56) References Cited

U.S. PATENT DOCUMENTS

| | | | |
|---|---|---|---|
| 2009/0316971 A1* | 12/2009 | Song | G06T 7/246 |
| | | | 382/131 |
| 2011/0044524 A1 | 2/2011 | Wang et al. | |
| 2012/0121153 A1* | 5/2012 | Xue | G06T 5/002 |
| | | | 382/131 |
| 2013/0089271 A1* | 4/2013 | Boernert | G01N 24/08 |
| | | | 382/274 |
| 2015/0323637 A1 | 11/2015 | Beck et al. | |
| 2016/0035091 A1* | 2/2016 | Kubassova | G06T 7/0012 |
| | | | 382/131 |

OTHER PUBLICATIONS

Sumbul et al "Improved Time Series Reconstruction for Dynamic Magnetic Resonance Imaging" IEEE Transactions on Medical Imaging, vol. 28, No. 7, Jul. 2009 p. 1093-1104.
Lebel et al "Highly Accelerated Dynamic Contast Enchanced Imaging" Magnetic Reson. in Med. vol. 71, p. 635-644 (2014).
Gamper et al "Compressed Sensing in Dynamic MRI" Magnetic Resonance in Med. vol. 59, p. 365-373 (2008).
Gdaniec et al "Joint Reconstruction of DCE Abdominal Images" In Proceedings of the 22nd Annual meeting of the ISMRM. 1546 (2014).
Lustig et al "Sparse MRI: The Application of Compressed Sensing for Rapid MR Imaging" Magnetic Resonance in Med. 58 p. 1182-1195 (2007).
D0nglai Huo et al: "Turboprop IDEAL: A Motion-Resistant Fat-Water Separation Technique", Magnetic Res0nance in Medicine,vol. 61, Dec. 18, 2008 (Dec. 18, 2008),pp. 188-195.
Dixon "Simple Proton Spectroscopic Imaging" Radiology Mag. Oct. 1984.
Gallichan et al "FatNavs: Exploiting the Natural Sparsity of Head Fat Images for High Resolution Motion Navigation at Very High Acceleration Factors" Proc. Intl. Soc. Mag. Reson. Med 21 p. 0309 (2013).

* cited by examiner

METHOD OF IMPROVED MULTIPLE-PHASE DYNAMIC CONTRAST-ENHANCED MAGNETIC RESONANCE IMAGING WITH MOTION CORRECTION USING WATER/FAT SIGNAL SEPARATION

CROSS REFERENCE TO RELATED APPLICATIONS

This application is a U.S. national phase application of International Application No. PCT/IB2015/052354, filed on Mar. 31, 2015, which claims the benefit of U.S. provisional Application Ser. No. 61/980,668 filed on Apr. 17, 2014 and is incorporated herein by reference.

FIELD OF THE INVENTION

The invention pertains to a method of operating a magnetic resonance imaging system with regard to acquiring multiple-phase dynamic contrast-enhanced magnetic resonance images, and a magnetic resonance imaging system being operated by employing such a method.

BACKGROUND OF THE INVENTION

In the art of magnetic resonance imaging it is known to employ dynamic contrast-enhanced (DCE) imaging for obtaining physiological information like organ functions and perfusion, for instance by administering a contrast agent to a subject of interest, usually a patient, for tumor assessment. Several types of contrast agents and ways of administering are known in the art. Standard clinical practice is to acquire one magnetic resonance image or more images before administering the contrast agent (pre-contrast), and to acquire images at a specified number of phases after administering the contrast agent (post contrast), for instance at the arterial phase, portal venous phase, delayed venous phase and at equilibrium.

SUMMARY OF THE INVENTION

Motion artifacts due to respiratory motion of the subject of interest can degrade image quality. Therefore, data are preferably acquired during a series of breath-holds. An acquisition during multiple breath-holds of the subject of interest might result in spatial displacement of the images, because the previous state of motion is not exactly achieved, and also because the patient might be in stress after the contrast agent has been administered.

Another issue that may arise during the acquisition of the magnetic resonance images is insufficient breath-hold capability of the subject of interest. This especially occurs during the arterial phase, which is crucial, for instance, for a differentiation of lesions.

Motion of the subject of interest occurring between consecutively acquired magnetic resonance images and a limited reproducibility of a required breath-hold position may thus result in degraded support for a diagnostic assessment.

It is therefore desirable to reduce the above-mentioned artifacts, to obtain consistent magnetic resonance image data, to improve time resolution of the acquired magnetic resonance images, in particular for post-contrast phases.

It is therefore an object of the invention to provide a method of operating a magnetic resonance imaging system with regard to acquiring multiple-phase dynamic contrast-enhanced magnetic resonance images with at least one of improved time resolution, improved independency of the ability of the subject of interest to hold breath and reduced effort and/or improved accuracy for magnetic resonance image reconstruction.

In one aspect of the present invention, the object is achieved by a method of operating a magnetic resonance imaging system with regard to acquiring multiple-phase dynamic contrast-enhanced magnetic resonance images, the magnetic resonance imaging system being configured for acquiring magnetic resonance images of at least a portion of a subject of interest. The method comprises steps of acquiring at least a first set of magnetic resonance image data prior to administering a contrast agent to the subject of interest, by employing a water/fat magnetic resonance signal separation technique, determining a first image of the spatial distribution of fat of at least the portion of the subject of interest from the first set of magnetic resonance image data, acquiring at least a second set of magnetic resonance image data of at least the portion of the subject of interest after administering the contrast agent to the subject of interest, by employing a water/fat magnetic resonance signal separation technique, determining at least a second image of the spatial distribution of fat of at least the portion of the subject of interest from the second set of magnetic resonance image data, and applying an image registration method to at least the second image of the spatial distribution of fat with reference to the first image of the spatial distribution of fat for correcting a potential motion of the subject of interest having occurred in the time between acquiring the first set of magnetic resonance image data and acquiring at least the second set of magnetic resonance image data.

The term "dynamic magnetic resonance imaging", as used in this application, shall be understood particularly as acquiring a magnetic resonance signal with two or three spatial coordinates and time as an additional dimension. In an appropriate transform domain, dynamic magnetic resonance images may have a sparse representation.

The phrase "water/fat magnetic resonance signal separation technique", as used in this application, shall be understood particularly to encompass methods known in the art of clinical magnetic resonance imaging for discriminating and separating the fat signal portion and the water signal portion in acquired magnetic resonance images.

The phrase "image registration", as used in this application, shall be understood particularly as a technique of transforming two different sets of image data into one coordinate system. Image registration techniques are commonly known in medical imaging and are commercially available (e.g. MATLAB® module by MathWorks®). The registration transformation is usually determined by optimizing a similarity measure calculated from the different sets of image data. In particular, the phrase "image registration method" shall encompass intensity-based and/or feature-based methods, rigid and/or non-rigid image registration as well as local correlation methods and/or registration techniques based on mutual information. Other image registration techniques that appear suitable to the person skilled in the art may as well be applied.

The invention is based on the concept that the spatial distribution of fat as determined from the first set of magnetic resonance image data and the spatial distribution of fat as determined from at least the second set of magnetic resonance image data are congruent and can be brought to alignment with high precision by applying an image registration method, as the magnetic resonance signal corresponding to the fat in the portion of the subject of interest is unaffected by the administering of the contrast agent.

An advantage of the invention lies in that any motion of the subject of interest occurring between a point in time of acquiring the first set of magnetic resonance image data and a point in time of acquiring at least the second set of magnetic resonance image data can be precisely corrected for despite the fact that the magnetic resonance image has changed because of the administering of the contrast agent.

Preferably, the sets of magnetic resonance image data are acquired during breath-hold periods in the respiration of the subject of interest. In principle, however, they may also be acquired while the subject of interest is breathing in a regular breathing pattern.

In a preferred embodiment, the method further comprises a step of using the determined first image of the unaltered spatial distribution of fat as prior knowledge for image reconstruction of at least the second set of magnetic resonance image data acquired after administering the contrast agent.

By making use of the a priori-knowledge that the magnetic resonance signals received from the fat is common to the magnetic resonance data acquired in the different phases, and is not very much affected by the administering of the contrast agent to the subject of interest, a portion of the effort for image reconstruction can be saved by using the data from the determined first image of the spatial distribution of fat as prior knowledge.

In another preferred embodiment, the method comprises steps of acquiring a plurality of sets of magnetic resonance image data after administering the contrast agent, and using the determined first image of the spatial distribution of fat as prior knowledge for image reconstruction of each set of magnetic resonance image data of the plurality of sets of magnetic resonance image data acquired after administering the contrast agent.

In this way, a substantial amount of effort for image reconstruction can be saved and the image reconstruction can be expedited.

In yet another embodiment of the method, the water/fat magnetic resonance signal separation technique is based on the difference in the Larmor frequencies of excited nuclei due to chemical shift. In this particular case, the chemical shift is the difference of the resonance frequencies of 3.5 ppm of protons bound in water versus protons bound in fat. Preferably, the water/fat magnetic resonance signal separation technique is based on the Dixon method, which is known in the art and is first described in the article by Dixon, W. T., "*Simple Proton Spectroscopic Imaging*", Radiology 153:189 (1984). Some embodiments of the Dixon method require acquiring more than one set of magnetic resonance image data, for instance an "in-phase" image set and an "opposed-phased" image set (the terms "in-phase" and "oppose-phased" describing the relation between the spin phases of protons bound in water and protons bound in fat), from which separate fat and water images can be calculated. It shall be understood that the image data required for one water/fat magnetic resonance signal separation approach are considered as acquiring one set of magnetic resonance image data. In this way, images of the spatial distribution of fat of at least the portion of the subject of interest can readily be obtained.

In another preferred embodiment, the method further comprises steps of obtaining, from determining the first image of the spatial distribution of fat of at least the portion of the subject of interest from the first set of magnetic resonance image data, a spatial distribution of a local static magnetic field strength $B_0$, reconstructing magnetic resonance images from any of the sets of magnetic resonance image data acquired after administrating the contrast agent to the subject of interest by using the obtained spatial distribution of the local static magnetic field strength.

The determined spatial distribution of the local static magnetic field strength can be utilized for correlating spin phase disturbances induced by variations of the static magnetic field strength that comply with the acquired magnetic resonance data. These correlations can advantageously be used for improving and/or expediting the image reconstruction process.

In yet another embodiment of the method, at least one of the second set of magnetic resonance image data or at least one set of magnetic resonance image data of the plurality of sets of magnetic resonance image data acquired after administering the contrast agent is obtained by employing a compressed sensing method.

In the art of magnetic resonance imaging, compressed sensing is known as a method of image reconstruction that provides a potentially significant reduction of acquisition time. Examples of compressed sensing magnetic resonance imaging are, for instance, given in the article by M. Lustig et al., "*Sparse MRI: The Application of Compressed Sensing for Rapid MR Imaging*", Magnetic Resonance in Medicine 58:1182-1195 (2007).

In this way, an improved temporal resolution for imaging a process of in-flowing/out-flowing contrast agent by magnetic resonance methods can be accomplished.

In another preferred embodiment, the method comprises a step of applying a filter to a set of magnetic resonance image data acquired prior to administering the contrast agent to the subject of interest, wherein the filter is equivalent to a high pass filter in k-space. As the main effect of the contrast agent can be expected at low frequencies in k-space, image reconstruction results for data acquired after administering the contrast agent can be improved with the help of the filtered signal acquired prior to administering the contrast agent.

In another aspect of the present invention, a magnetic resonance imaging system is provided that is configured for acquiring magnetic resonance images of at least a portion of a subject of interest.

Further, the magnetic resonance imaging system comprises an examination space provided to position at least the portion of the subject of interest within, a main magnet configured for generating a static magnetic field $B_0$ in the examination space, a magnetic gradient coil system configured for generating gradient magnetic fields superimposed to the static magnetic field $B_0$, at least one radio frequency antenna device that is provided for applying a radio frequency excitation field $B_1$ to nuclei of or within the portion of the subject of interest for magnetic resonance excitation, at least one radio frequency antenna device that is configured for receiving magnetic resonance signals from the nuclei of or within the portion of the subject of interest that have been excited by applying the radio frequency excitation field $B_1$, a control unit for controlling functions of the magnetic resonance imaging system, an image processing unit configured for processing magnetic resonance signals to determine magnetic resonance images of at least the portion of the subject of interest from the received magnetic resonance signals.

The control unit is configured to carry out steps of an embodiment of the methods disclosed herein or a combination thereof.

In yet another aspect of the present invention, a software module is provided for carrying out an embodiment of any of the methods disclosed above or a combination thereof, of operating a magnetic resonance imaging system with regard to acquiring multiple-phase dynamic contrast-enhanced magnetic resonance images. The method steps to be conducted are converted into a program code of the software module, wherein the program code is implementable in a memory unit of the magnetic resonance imaging system and is executable by a processor unit of the magnetic resonance imaging system. The processor unit may be the processor unit of the control unit that is customary for controlling functions of a magnetic resonance imaging system. The processor unit may, alternatively or supplementary, be another processor unit that is especially assigned to execute at least some of the method steps.

The software module can enable a robust and reliable execution of the method and can allow for a fast modification of method steps.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
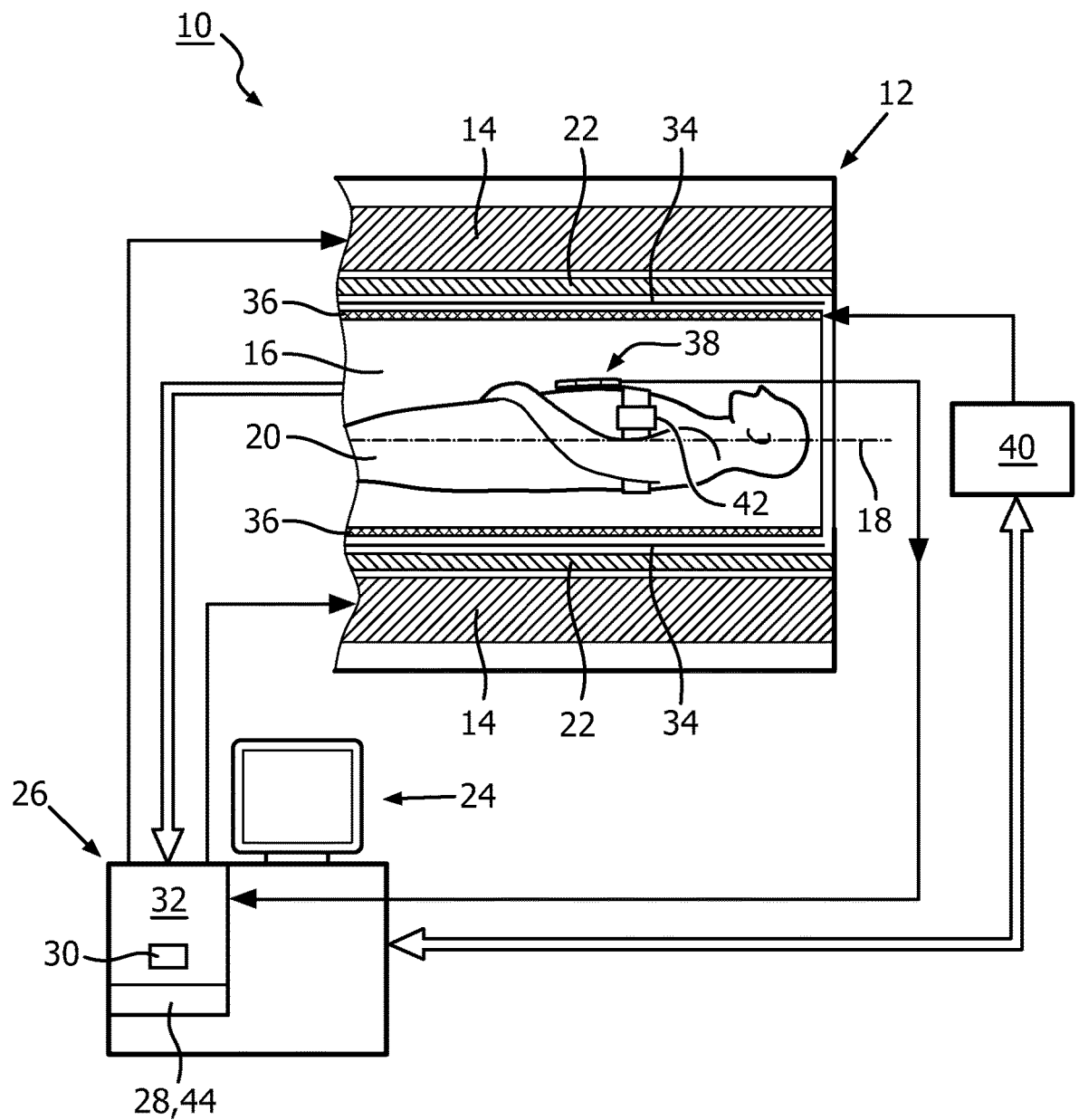
FIG. 1 is a schematic illustration of a part of an embodiment of a magnetic resonance imaging system in accordance with the invention.

FIG. 1 shows a schematic illustration of a part of an embodiment of a magnetic resonance imaging system 10 configured for acquiring magnetic resonance images of at least a portion of a subject of interest 20, usually a patient. The magnetic resonance imaging system 10 comprises a scanning unit 12 having a main magnet 14. The main magnet 14 has a central bore that provides an examination space 16 around a center axis 18 for the subject of interest 20 to be positioned within, and is further provided for generating a static magnetic field $B_0$ at least in the examination space 16. For clarity reasons, a customary table for supporting the subject of interest 20 has been omitted in FIG. 1. The static magnetic field $B_0$ defines an axial direction of the examination space 16, aligned in parallel to the center axis 18. It is appreciated that the invention is also applicable to any other type of magnetic resonance imaging systems providing an examination region within a static magnetic field.

Further, the magnetic resonance imaging system 10 comprises a magnetic gradient coil system 22 provided for generating gradient magnetic fields superimposed to the static magnetic field $B_0$. The magnetic gradient coil system 22 is concentrically arranged within the bore of the main magnet 14.

The magnetic resonance imaging system 10 comprises a control unit 26 configured to control functions of the magnetic resonance imaging system 10. The control unit 26 includes a human interface device 24 including a monitor unit having a touch-sensitive screen.

Furthermore, the magnetic resonance imaging system 10 includes a radio frequency antenna device 36 designed as a whole-body coil that is provided for applying a radio frequency excitation field $B_1$ to nuclei of or within the subject of interest 20 for magnetic resonance excitation during radio frequency transmit time periods to excite the nuclei of or within the subject of interest 20 for the purpose of magnetic resonance imaging. To this end, radio frequency power is fed, controlled by the control unit 26, from a radio frequency transmitter 40 to the whole-body coil. The whole-body coil has a center axis and, in the operational state, is arranged concentrically within the bore of the main magnet 14 such that the center axis of the whole-body coil and the center axis 18 of the scanning unit 12 coincide. As is well known in the art, a cylindrical metal radio frequency shield 34 is arranged concentrically between the magnetic gradient coil system 22 and the whole-body coil.

Moreover, the magnetic resonance imaging system 10 comprises a plurality of radio frequency antenna devices 38 provided for receiving magnetic resonance signals from the nuclei of or within the subject of interest 20 that have been excited by applying the radio frequency excitation field $B_1$. The radio frequency antenna devices 38 of the plurality of radio frequency antenna devices 38 are designed as an array of local coils that are intended to be positioned proximal to a region of the subject of interest 20 to be imaged, namely the liver. The local coils are configured for receiving magnetic resonance signals from the excited nuclei of or within the portion of the subject of interest 20 to be imaged during radio frequency receiving time periods which are distinct from the radio frequency transmit time periods.

Furthermore, the magnetic resonance imaging system 10 comprises an image processing unit 32 provided for processing magnetic resonance signals to determine magnetic resonance images of at least the portion of the subject of interest 20 from the received magnetic resonance signals.

The magnetic resonance imaging system 10 further comprises a respiration monitoring device 42. The respiration monitoring device 42 includes a respiration sensor that, in an operational state, is attached to the thorax of the subject of interest 20 and is held by a belt which is wound around the thorax. It is appreciated by the one skilled in the art that other types of respiration monitoring devices are as well employable. The respiration monitoring device 42 is configured to provide the control unit 26 with an output signal whose level represents a respiration state of the subject of interest 20. To this end, an output line of the respiration monitoring device 42 is connected to the control unit 26. The control unit 26 of the magnetic resonance imaging system 10 is configured for receiving an output signal from the respiration monitoring device 42. The output signal is displayed on the monitor unit of the human interface device 24. In this way, a breathing pattern and, in particular, breath-hold periods can be checked by an operator.

Magnetic resonance image acquisition during individual breath-holds is performed using a breath-hold adaptive sampling pattern. As an alternative, a related fast sampling scheme could be employed. In the mentioned adaptive sampling pattern, the spatial resolution of the magnetic resonance image is automatically adapted during image acquisition, and is combined with the output signal of the respiration monitoring device 42 in such a way that the acquisition of the magnetic resonance image is terminated at breathing onset. Premature onset of breathing results in an incomplete set of magnetic resonance image data. The adaptive sampling pattern is designed to ensure incoherence at every instance in time, which enables to apply a compressed sensing reconstruction method.

Figure 2:
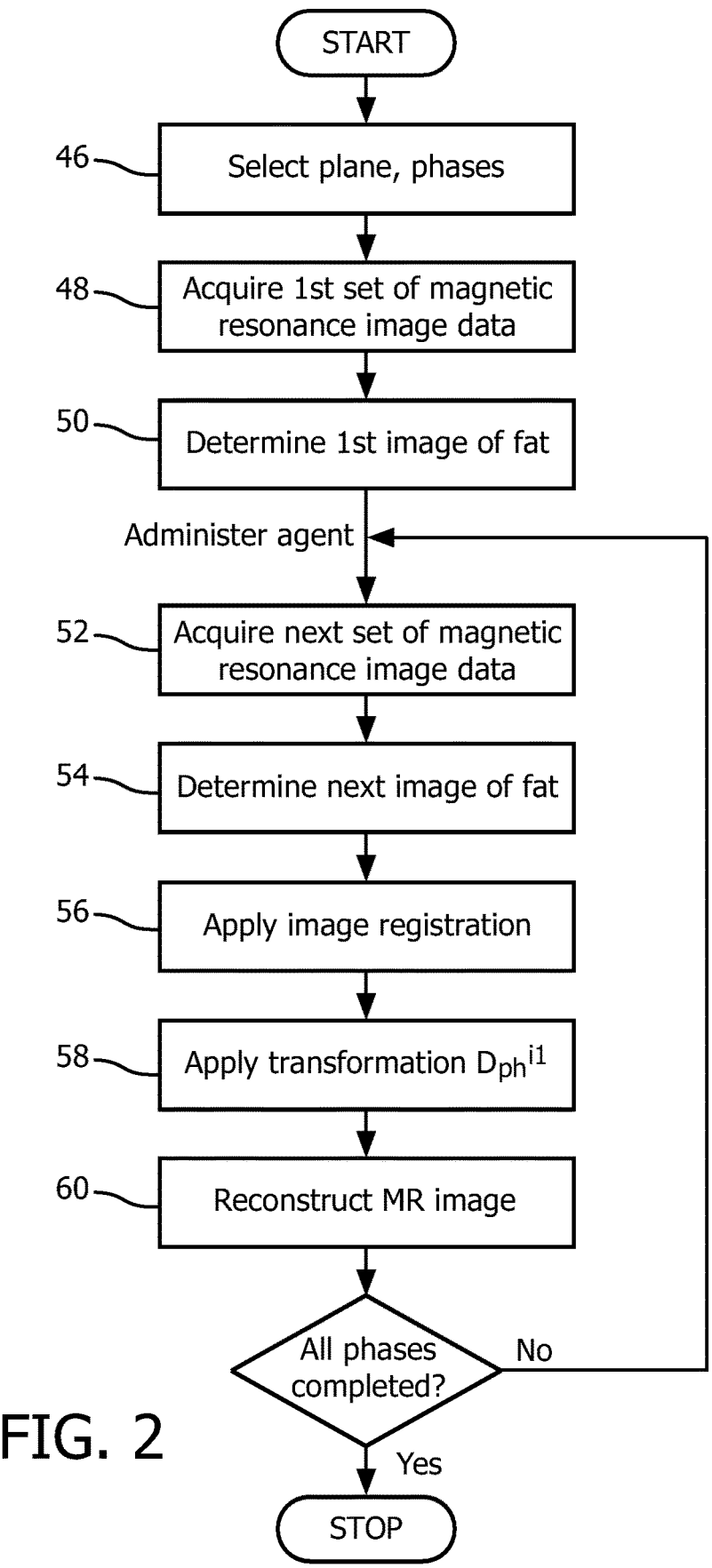
FIG. 2 shows a flowchart of a method in accordance with the invention of operating the magnetic resonance imaging system pursuant to FIG. 1.

In the following, an embodiment of a method of operating the magnetic resonance imaging system 10 with regard to acquiring multiple-phase dynamic contrast-enhanced magnetic resonance images during breath-hold periods in the respiration of the subject of interest 20 is described. A principal flow chart of the method is given in FIG. 2. In preparation of operating the magnetic resonance imaging system 10, it shall be understood that all involved units and devices are in an operational state and configured as illustrated in FIG. 1.

In order to be able to carry out the method as a specific operation of the magnetic resonance imaging system 10, the control unit 26 comprises a software module 44 (FIG. 1). The method steps to be conducted are converted into a program code of the software module 44, wherein the program code is implementable in a memory unit 28 of the control unit 26 and is executable by a processor unit 30 of the control unit 26.

In a preparatory step 46, via the touch-sensitive screen of the human interface device 24, the operator selects a transversal plane of the portion of the subject of interest 20 to be imaged and the number of phases to be imaged from the portion of the subject of interest 20 before and after administering a contrast agent. In a preceding preparatory calibration measurement, threshold signal levels of the output signal of the respiration monitoring device 42 which correspond to a respiration breath-hold at full inspiration of the subject of interest 20 have been determined. A minimum value of the threshold signal level is stored in the memory unit 28 of the control unit 26.

In a first step 48 of the method, prior to administering the contrast agent to the subject of interest 20, a first set of magnetic resonance image data $x_{pre}$ is acquired during a breath-hold period in the respiration of the subject of interest 20 at two different echo times.

From the acquired first set of magnetic resonance image data $x_{pre}$, a first image of the spatial distribution of fat $I_{pre}$ of at least the portion of the subject of interest 20 is determined in another step 50 from a full image reconstruction, by employing a water/fat magnetic resonance signal separation technique that is based on the Dixon method, wherein magnetic resonance image data are acquired at one echo time or more than one different echo times. In this particular embodiment, the first set of magnetic resonance image data $x_{pre}$ is acquired at two different echo times. The Dixon method, well known in the art, is based on the difference in the Larmor frequencies of excited nuclei, in this embodiment given by protons, due to chemical shift.

In the next step then, a gadolinium-based contrast agent is administered to the subject of interest 20 as an intravenous bolus injection.

In another step 52 of the method, after administering the contrast agent to the subject of interest 20, a second set of magnetic resonance image data $x_2$ of at least the portion of the subject of interest 20 is acquired in the arterial phase and during another breath-hold period in the respiration of the subject of interest 20, wherein the second set of magnetic resonance image data $x_2$ is acquired at two (alternatively three) different echo times.

From the acquired second set of magnetic resonance image data $x_2$, a second image of the spatial distribution of fat $I_2^{ph}$ of at least the portion of the subject of interest 20 is determined in another step 54 from an iterative image reconstruction using the water/fat magnetic resonance signal separation technique based on the Dixon method, as will be described later on.

In contrast to the excited protons bound in water, the magnetic resonance image signal stemming from the excited protons bound in the fat tissue of at least a portion of the subject of interest 20 is not affected by the administered contrast agent. Therefore, the image of the spatial distribution of fat $I_{pre}$ obtained from the first set of magnetic resonance image data $x_{pre}$ and the image of the spatial distribution of fat $I_2^{ph}$ obtained from the second set of magnetic resonance image data $x_2$ are substantially congruent, and a transformation function $D_{ph}{}^{21}$ exists that minimizes a difference between the first image of the spatial distribution of fat $I_{pre}$ and the second image of the spatial distribution of fat $I_2^{ph}$. The difference is understood with regard to a suitable, specified mathematical norm.

The control unit 26 of the magnetic resonance imaging system 10 includes a rigid-type image registration using software residing in the memory unit 28 of the control unit 26 and being executable by the processor unit 30 of the control unit 26. By applying the image registration method to the second image of the spatial distribution of fat $I_2^{ph}$ with reference to the first image of the spatial distribution of fat $I_{pre}$ via the control unit 26 in a next step 56 of the method, the transformation $D_{21}{}^{ph}$ is determined.

Then, in a following step 58 of the method, the determined transformation $D_{21}{}^{ph}$ is applied to the acquired second set of magnetic resonance image data $x_2$ for correcting a potential motion of the subject of interest 20 having occurred in the time between acquiring the first set of magnetic resonance image data $x_{pre}$ and the second set of magnetic resonance image data $x_2$.

In the phase after administering the contrast agent to the subject of interest 20, much narrower time constraints for image reconstruction exist than before administering the contrast agent. In a following step 60 of the method, the determined first image of the spatial distribution of fat $I_{pre}$ is used as prior knowledge for applying image reconstruction to the second set of magnetic resonance image data $x_2$ which has been acquired after administering the contrast agent.

The second set of magnetic resonance image data $x_2$ is thereby obtained by employing parallel imaging or a compressed sensing method for image reconstruction, wherein prior knowledge is given by the existing determined first image of the spatial distribution of fat $I_{pre}$, which allows for potential higher under-sampling for the magnetic resonance images to be acquired after administering the contrast agent.

In the same manner as described above, a third set of magnetic resonance image data $x_3$ is acquired in the portal venous phase and during another breath-hold period in the respiration of the subject of interest 20, wherein magnetic resonance data are acquired at two (alternatively three) different echo times.

The third set of magnetic resonance image data $x_3$ is obtained by employing parallel imaging or the method of compressed sensing for image reconstruction, wherein the already existing starting basis, given by the determined first image of the spatial distribution of fat $I_{pre}$, again allows applying the under-sampling method as described before.

From the acquired third set of magnetic resonance image data $x_3$, a third image of the spatial distribution of fat $I_3^{ph}$ of at least the portion of the subject of interest 20 is determined using the water/fat magnetic resonance signal separation technique based on the Dixon method.

By applying the image registration method to the third image of the spatial distribution of fat $I_3^{ph}$ with reference to the first image of the spatial distribution of fat $I_{pre}$ via the control unit 26, a transformation $D_{31}^{ph}$ is obtained.

Then, the determined transformation $D_{31}^{ph}$ is applied to the acquired third set of magnetic resonance image data $x_3$ for correcting a potential motion of the subject of interest 20 having occurred in the time between acquiring the second magnetic resonance image $x_2$ and the third magnetic resonance image $x_3$.

In the above-described manner, also a fourth set and a fifth set of magnetic resonance image data $x_4$, $x_5$ of at least the portion of the subject of interest 20 are acquired in the delayed venous phase and in the phase of equilibrium, respectively, during other breath-hold periods in the respiration of the subject of interest 20, wherein the magnetic resonance data are acquired at two (alternatively three) different echo times.

The fourth and the fifth set of magnetic resonance image data $x_4$, $x_5$ are obtained by employing the method of compressed sensing for image reconstruction, with the determined first image of the spatial distribution of fat $I_{pre}$ as starting basis, and by applying the under-sampling method as described above.

From the acquired fourth and fifth set of magnetic resonance image data $x_4$, $x_5$, respectively, a fourth image of the spatial distribution of fat $I_4^{ph}$ and a fifth image of the spatial distribution of fat $I_5^{ph}$ of at least the portion of the subject of interest 20 are determined using the water/fat magnetic resonance signal separation technique based on the Dixon method.

Transformations $D_{41}^{ph}$ and $D_{51}^{ph}$ are determined by applying the image registration method to the fourth image of the spatial distribution of fat $I_4^{ph}$ and the fifth image of the spatial distribution of fat $I_5^{ph}$, respectively, with reference to the first image of the spatial distribution of fat $I_{pre}$, via the control unit.

In an alternative approach, the second to fifth set of magnetic resonance image data $x_2$ to $x_5$ acquired after administering the contrast agent to the subject of interest 20 are commonly obtained by employing a compressed sensing method for image reconstruction, wherein the determined first image of the spatial distribution of fat $I_{pre}$ is employed as prior knowledge for reconstruction, and an affine motion of the subject of interest 20 is involved for applying the registration method to the second to fifth image of the spatial distribution of fat $I_2^{ph}$ to $I_5^{ph}$.

By using the a priori-knowledge about the fat distribution being common to all spatial distributions of fat, and the a priori knowledge that the images of the spatial distribution of fat $I_{pre}$, $I_2^{ph}$ to $I_5^{ph}$ are associated by a smooth motion of the very same patient, an improved accuracy for image reconstruction can be accomplished and under-sampling artifacts can at least be reduced or potentially prevented.

Another approach for the image reconstruction from acquired magnetic resonance data can be described as an optimization of the following mathematical expression, to be executed for all numbers of index i, indicating the temporal phase, $$\min |\psi x_i|_1 + \lambda_1 |UFx_i - y_i|_2 + \lambda_2 |I_{pre} - D_{i1}^{ph} I_i^{ph}|_2 + \lambda_3 |HF(D_{i1}^{-1\,ph} x_{pre}) - H(y_i)|_2$$

with the following denotation:
$x_{pre}$ set of magnetic resonance image data acquired before administering contrast agent (first set)
$x_i$ i-th set of magnetic resonance image data acquired after administering contrast agent
$y_i$ k-space data representation of $x_i$
$\psi$ sparsifying transformation of compressed sensing method
U under-sampling operator
F Fourier transform operator
H high pass filter adapted to applicable domain, preferably represented by k-space mathematical p-norm
$|\ |_p$ mathematical p-norm
$\lambda_1$-$\lambda_3$ regularization parameters (real numbers)

The first term enforces sparsity of the acquired image in an adequate transform domain.

The second term of the expression ensures data consistency at locations in k-space that were acquired.

The third term of the expression considers the potential motion of the subject of interest 20, occurring between a point in time of acquiring the first set of magnetic resonance image data $x_{pre}$, and a point in time of acquiring the i-th set of magnetic resonance image data $x_i$.

The fourth term of the expression reflects similarity of high frequencies in an applicable domain, which is preferably represented by the k-space, from data acquired prior to administering the contrast agent and after administering the contrast agent.

The regularization parameters $\lambda_1$, $\lambda_2$, $\lambda_3$ can be inputted by the operator via the human interface device 24 as weighting factors. At least one of the regularization parameters $\lambda_1$, $\lambda_2$, $\lambda_3$ can be chosen as zero.

It is interesting to note that the concept described in the equation above could also be applied to appropriate subsets of the data with the ability to correct also for potential motion inconsistencies within the individual wash-in/wash-out phase data sets.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

| REFERENCE SYMBOL LIST | |
|---|---|
| 10 | magnetic resonance imaging system |
| 12 | scanning unit |
| 14 | main magnet |
| 16 | examination space |
| 18 | center axis |
| 20 | subject of interest |
| 22 | magnetic gradient coil system |
| 24 | human interface device |
| 26 | control unit |
| 28 | memory unit |
| 30 | processor unit |
| 32 | image processing unit |
| 34 | metal radio frequency shield |

-continued

REFERENCE SYMBOL LIST

| | |
|---|---|
| 36 | radio frequency antenna device (transmitting) |
| 38 | plurality of radio frequency antenna devices (receiving) |
| 40 | radio frequency transmitter |
| 42 | respiration monitoring device |
| 44 | software module |
| 46 | preparatory step |
| 48 | step of acquiring $1^{st}$ set of magnetic resonance image data |
| 50 | step of determining 1st image of spatial distribution of fat |
| 52 | step of of acquiring $2^{nd}$ set of magnetic resonance image data |
| 54 | step of determining $2^{nd}$ image of spatial distribution of fat |
| 56 | step of applying image registration method |
| 58 | step of applying determined transformation |
| 60 | step of using $1^{st}$ image of spatial distribution of fat for image reconstruction |
| $B_0$ | static magnetic field |
| $B_1$ | radio frequency excitation field |
| $I_{pre}$ | $1^{st}$ image of spatial distribution of fat |
| $I_i^{ph}$ | i-th image of the spatial distribution of fat |
| $x_{pre}$ | $1^{st}$ set of magnetic resonance image data |
| $x_i$ | i-th set of magnetic resonance image data |

The invention claimed is:

1. A method of operating a magnetic resonance imaging system with regard to acquiring multiple-phase dynamic contrast-enhanced magnetic resonance images, the magnetic resonance imaging system being configured for acquiring magnetic resonance images of at least a portion of a subject of interest, the method comprising:
acquiring a first set of magnetic resonance image data (xpre) of the at least a portion of the subject of interest prior to administering a contrast agent to the subject of interest;
determining a first image of a spatial distribution of fat (Ipre) of the at least a portion of the subject of interest from the first set of magnetic resonance image data (xpre) using a water/fat magnetic resonance signal separation technique;
acquiring a plurality of additional sets magnetic resonance image data (xi) of the at least a portion of the subject of interest after administering the contrast agent to the subject of interest;
determining a plurality of images of the spatial distribution of fat (Iiph) of the at least a portion of the subject of interest from the plurality of additional sets of magnetic resonance image data (xi) using the water/fat magnetic resonance signal separation technique;
applying an image registration method to each of the plurality of images of the spatial distribution of fat (Iiph) with reference to the first image of the spatial distribution of fat (Ipre) to determine transformations for minimizing differences between the plurality of images of the spatial distribution of fat (Iiph) and the first image of the spatial distribution of fat (Ipre); and
applying the determined transformations to the plurality of additional sets of magnetic resonance image data (xi) for correcting for motion of the subject of interest in magnetic resonance images reconstructed from the additional sets of magnetic resonance image data (xi), respectively, the motion having occurred in times between acquiring the first set of magnetic resonance image data (xpre) and acquiring the additional sets of magnetic resonance image data (xi).

2. The method of claim 1 wherein the water/fat magnetic resonance signal separation technique is based on a difference in Larmor frequencies of excited nuclei due to chemical shift.

3. The method of claim 1, wherein the additional sets of magnetic resonance image data (xi) acquired after administering the contrast agent are obtained using a compressed sensing method.

4. The method of claim 1, further comprising applying a filter to the first set of magnetic resonance image data (xpre) acquired prior to administering the contrast agent to the subject of interest, wherein the filter is equivalent to a high pass filter in k-space.

5. A magnetic resonance imaging system configured for acquiring magnetic resonance images of at least a portion of a subject of interest, comprising:
an examination space configured for positioning the at least a portion of the subject of interest within;
a main magnet configured for generating a static magnetic field in the examination space;
a magnetic gradient coil system configured for generating gradient magnetic fields superimposed to the static magnetic field;
at least one transmitting radio frequency antenna device configured for applying a radio frequency excitation field to nuclei of or within the at least a portion of the subject of interest for magnetic resonance excitation;
at least one receiving radio frequency antenna device configured for receiving magnetic resonance signals from the nuclei of or within the portion of the subject of interest that have been excited by applying the radio frequency excitation field;
a controller, comprising memory and at least one processor, configured for controlling functions of the magnetic resonance imaging system, wherein the memory stores instructions that, when executed by the at least one processor, cause the at least one processor to perform a process comprising:
receiving a first set of magnetic resonance image data (xpre) of the at least a portion of the subject of interest acquired prior to administering a contrast agent to the subject of interest;
determining a first image of a spatial distribution of fat (Ipre) of the at least a portion of the subject of interest from the first set of magnetic resonance image data (xpre) using a water/fat magnetic resonance signal separation technique;
receiving a plurality of additional sets of magnetic resonance image data (xi) of the at least a portion of the subject of interest acquired after administering the contrast agent to the subject of interest;
determining a plurality of images of the spatial distribution of fat (Iiph) of the at least a portion of the subject of interest from the plurality of additional sets of magnetic resonance image data (xi) using the water/fat magnetic resonance signal separation technique;
applying an image registration method to each of the plurality of images of the spatial distribution of fat (Iiph) with reference to the first image of the spatial distribution of fat (Ipre) to determine transformations for minimizing differences between the plurality of images of the spatial distribution of fat (Iiph) and the first image of the spatial distribution of fat (Ipre); and
applying the determined transformations to the received plurality of additional sets of magnetic resonance image data (xi) for correcting for motion of the subject of interest in magnetic resonance images reconstructed from the additional sets of magnetic resonance image data (xi), respectively, the motion having occurred in times between acquiring the first set of magnetic resonance image data (xpre) and acquiring the additional sets of magnetic resonance image data (xi).

6. The system of claim 5, wherein the water/fat magnetic resonance signal separation technique is based on a difference in Larmor frequencies of excited nuclei due to chemical shift.

7. The system of claim 5, wherein the additional sets of magnetic resonance image data (xi) acquired after administering the contrast agent are obtained using a compressed sensing method.

8. The system of claim 5, wherein the process performed by the at least one processor further comprises:
  applying a filter to the first set of magnetic resonance image data (xpre) acquired prior to administering the contrast agent to the subject of interest, wherein the filter is equivalent to a high pass filter in k-space.

9. A non-transitory computer readable medium storing instructions for controlling acquisition of multiple-phase dynamic contrast-enhanced magnetic resonance images of at least a portion of a subject of interest, the instructions, when executed by a computer processor, causing the computer processor to perform a method comprising:
  receiving a first set of magnetic resonance image data (xpre) of the at least a portion of the subject of interest acquired prior to administering a contrast agent to the subject of interest;
  determining a first image of a spatial distribution of fat (Ipre) of the at least a portion of the subject of interest from the first set of magnetic resonance image data (xpre) using a water/fat magnetic resonance signal separation technique;
  receiving a plurality of additional sets of magnetic resonance image data (xi) of the at least a portion of the subject of interest acquired after administering the contrast agent to the subject of interest;
  determining a plurality of images of the spatial distribution of fat (Iiph) of the at least a portion of the subject of interest from the plurality of additional sets of magnetic resonance image data (xi) using the water/fat magnetic resonance signal separation technique;
  applying an image registration method to each of the plurality of images of the spatial distribution of fat (Iiph) with reference to the first image of the spatial distribution of fat (Ipre) to determine transformations for minimizing differences between the plurality of images of the spatial distribution of fat (Iiph) and the first image of the spatial distribution of fat (Ipre); and
  applying the determined transformations to the received plurality of additional sets of magnetic resonance image data (xi) to correct for motion of the subject of interest in magnetic resonance images reconstructed from the additional sets of magnetic resonance image data (xi), respectively, the motion having occurred in times between acquiring the first set of magnetic resonance image data (xpre) and acquiring the additional sets of magnetic resonance image data (xi).

* * * * *